(12) United States Patent
Tsujimura

(10) Patent No.: US 10,052,319 B2
(45) Date of Patent: Aug. 21, 2018

(54) MEDICAMENT FOR TREATING MENTAL AND BEHAVIOURAL DISORDERS

(71) Applicant: Sumitomo Dainippon Pharma Co., Ltd., Osaka (JP)

(72) Inventor: Tsuyoshi Tsujimura, Osaka (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 13/827,655

(22) Filed: Mar. 14, 2013

(65) Prior Publication Data

US 2013/0289277 A1 Oct. 31, 2013

Related U.S. Application Data

(60) Provisional application No. 61/638,725, filed on Apr. 26, 2012.

(30) Foreign Application Priority Data

Apr. 26, 2012 (JP) .................................. 2012-100816

(51) Int. Cl.
*A61K 31/496* (2006.01)
(52) U.S. Cl.
CPC ................................. *A61K 31/496* (2013.01)
(58) Field of Classification Search
CPC ................................................... A61K 31/496
USPC ......................................................... 544/368
See application file for complete search history.

(56) References Cited

U.S. PATENT DOCUMENTS

| 5,532,372 A | 7/1996 | Saji et al. |
| 2012/0238552 A1* | 9/2012 | Perry et al. ................... 514/220 |

FOREIGN PATENT DOCUMENTS

JP 5-17440 A 1/1993

OTHER PUBLICATIONS

Kimberly A Pesaturo, Risperidone (Risperdal) for Management of Autistic Disorder, Am Fam Physician. Jun. 15, 2009;79(12):1104-1107.*
Ludovic Samalin, Marion Garnier, and Pierre-Michel Llorca, Clinical potential of lurasidone in the management of schizophrenia, Therapeutics and Clinical Risk Management 2011:7 239-250.*
Laura C. Politte & Christopher J. McDougle, Atypical antipsychotics in the treatment of children and adolescents with pervasive developmental disorders, Psychopharmacology (2014) 231:1023-1036.*
Baird, Gillian et al., "Diagnosis of Autism," British Medical Journal, 327, 488-493 (2003).
McCracken, M.D., James T. et al., "Risperidone in Children with Autism and Serious Behavioral Problems," The New England Journal of Medicine, 347(5), 314-321 (2002).
Meyer, Jonathan M. et al., "Lurasidone: a new drug in development for schizophrenia," Expert Opinion on Investigation Drugs, 18(11), 1715-1726 (2009).
Muglia, Pierandrea, "From Genes to Therapeutic Targets for Psychiatric Disorders—What to Expect?," Current Opinion in Pharmacology, Oct. 2011, vol. 11, 563-571.
Owen, Randall et al., "Aripiprazole in the Treatment of Irritability in Children and Adolescents With Autistic Disorder," Pediatrics, 124(6), 1533-1540 (2009).
The International Search Report and the Written Opinion of the International Searching Authority for PCT/JP2013/058473 dated May 21, 2013.
R. Corbett et al., "Antipsychotic agents antagonize non-competitive N-methyl-D-aspartate antagonist-induced behaviros", Psychopharmacology, 1995, 120:67-74.
T. Sugiyama, "What Is Autism Spectrum", Japanese Journal of Molecular Psychiatry, 2011, vol. 11, No. 4, p. 264-268 (with partial English-translation).
M. Horiguchi et al., "Interaction of mGlu$_{2/3}$ agonism with clozapine and lurasidone to restore novel object recognition in subchronic phencyclidine-treated rats", Psychopharmacology, 2011, vol. 217, No. 1, p. 13-24.
"Autism Spectrum Disorder", Merck Manual 18th Ed., Japanese Ver., 2007, p. 2641-2643 (with partial English-translation).
M. Sasaki, "Drug Therapy in Autism", Japanese Journal of Pediatrics, 2008, vol. 61, No. 12, p. 2399-2403 (with partial English-translation).

* cited by examiner

*Primary Examiner* — Sarah Pihonak
*Assistant Examiner* — Jason Deck
(74) *Attorney, Agent, or Firm* — Oblon, McClelland, Maier & Neustadt, L.L.P.

(57) ABSTRACT

The present invention relates to a medicament comprising lurasidone or a pharmaceutically acceptable acid addition salt thereof for treating pervasive developmental disorders and a method of the treatment thereof.

3 Claims, 2 Drawing Sheets

MEDICAMENT FOR TREATING MENTAL AND BEHAVIOURAL DISORDERS

TECHNICAL FIELD

The present invention relates to a medicament for treating pervasive developmental disorders and a method of the treatment, in detail, a novel medicament for treating autism and a novel method of the treatment.

BACKGROUND ART

Lurasidone [chemical name: (3aR,4S,7R,7aS)-2-{(1R,2R)-2-[4-(1,2-benzisothiazol-3-yl)piperazin-1-ylmethyl]cyclo-hexylmethyl}hexahydro-4,7-methano-2H-isoindole-1,3-dione] of the following formula is a compound having a pharmacological activity as an antipsychotic agent, which is characteristic of a high affinity for dopamine $D_2$, serotonin 5-$HT_{1A}$, 5-$HT_{2A}$, 5-$HT_7$, and noradrenaline $\alpha_{2C}$ receptors, and characteristic of minimal to no affinity for histamine $H_1$ and muscarinic $M_1$ receptors. Lurasidone possesses antipsychotic effects, antidepressant- and anxiolytic-like effects, and pharmacological profiles with potentially-reduced liability for extrapyramidal and CNS depressant side effects, which is expected to be used for the treatment of schizophrenia and bipolar disorder (Patent Reference 1, Non-patent Reference 1).

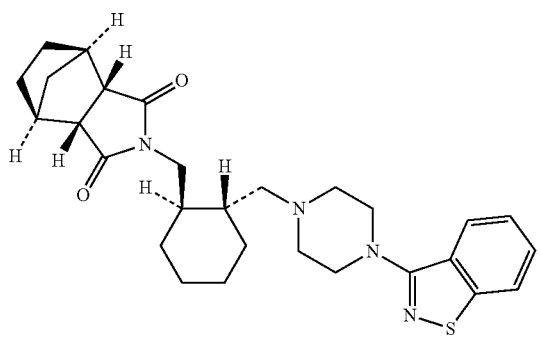 [SMILES: O=C1[C@@H]2[C@H]3CC[C@H](C3)[C@@H]2C(=O)N1C[C@@H]1CCCC[C@H]1CN1CCN(c2nsc3ccccc23)CC1]

International Statistical Classification of Diseases and Related Health Problems (also known as "ICD-10") includes "Mental and behavioural disorders" (F00-F99) as a category in Chapter V which further includes "Pervasive developmental disorders" (F84) as a small-classified disease in a subcategory "Disorders of psychological development" (F80-F89). According to ICD-10, the pervasive developmental disorders are furthermore classified into 8 diseases, i.e., childhood autism ("autism" in ICD-10), atypical autism, Rett's syndrome (Rett syndrome), other childhood disintegrative disorder, overactive disorder associated with mental retardation (or intellectual disability) and stereotyped movements, Asperger's syndrome (Asperger syndrome), other pervasive developmental disorders, and unspecified pervasive developmental disorder. Amongst them, autism is a typical disease thereof, and it is sometimes used as a generic term thereof. Autism is characterized by the development of impairments in social adaptive function, impairments in communication, and perseveration of specific behavior/interest. In addition, patients of genetic and/or congenital diseases such as fragile X syndrome, congenital rubella syndrome, cytomegalic inclusion body disease, and phenylketonuria can develop an autism-like symptom.

The prevalence rate of autism is thought to be about 1%, and it is reported that the men's prevalence is three to nine times higher than the women's, i.e., it is known that there is some difference on the incidence rate of the disease between men and women (Non-patent Reference 2). Patients of autism generally have core symptoms such as impairments in social adaptive function and impairments in communication, and peripheral symptoms such as abnormal repetitive behavior, hyperactivity, impulsivity, and irritability. It is known that autism is developed during childhood, but its core symptoms (impairments in social adaptive function and impairments in communication) can still continue even in adulthood. Thus, it is indicated that patients of autism have social disadvantages.

The current method for treating autism includes various programs such as TEACCH (Treatment and Education of Autistic and related Communication handicapped CHildren), and Social Skills Training (SST), which are based on educational treatment. The purpose of these programs is to promote the communication in patients of autism and relieve a difficulty in their social lives, but there is no curative treatment. The drug therapy for autism is only a symptomatic therapy with a drug useful for peripheral symptoms thereof. For example, in order to treat irritability which is one of transient peripheral symptoms in autism, some drugs such as aripiprazole and risperidone are used as a symptomatic therapy (Non-patent References 3 and 4). However, there is no useful drug for impairments in social adaptive function or impairments in communication which are core symptoms in autism.

PRIOR ART

Patent Reference

[Patent Reference 1] JP 5 (1993)-17440 A (U.S. Pat. No. 5,532,372 A)

Non-Patent Reference

[Non-patent Reference 1] Expert Opin. Investg. Drugs, 2009, 18(11), 1715-1726.
[Non-patent Reference 2] British Medical Journal, 2003, 327, 488-493.
[Non-patent Reference 3] N Engl J Med, 2002, 347(5), 314-321.
[Non-patent Reference 4] Pediatrics, 2009, 124(6), 1533-1540.

DISCLOSURE OF INVENTION

Problem to be Solved by the Invention

The purpose of the present invention is to provide a novel medicament for treating pervasive developmental disorders and a novel method thereof. In particular, the purpose is to provide a medicament and a method useful for treating autism. In more detail, the purpose is to provide a medicament and a method useful for treating core symptoms (impairments in social adaptive function and impairments in communication) in pervasive developmental disorders and autism.

Means to Solve the Problem

The present inventor has extensively studied to reach the above object and then have found that lurasidone or a pharmaceutically acceptable acid addition salt thereof of the present invention exhibits the therapeutic effect for pervasive developmental disorders and autism, in particular, the therapeutic effect for improving core symptoms (impairments in social adaptive function and impairments in communication) in pervasive developmental disorders and autism. Based upon the new findings, the present invention has been completed.

[1] A medicament for treating pervasive developmental disorders comprising lurasidone or a pharmaceutically acceptable acid addition salt thereof.

[2] The medicament of [1] wherein the pervasive developmental disorders are selected from the group consisting of autism, atypical autism, Rett's syndrome, other childhood disintegrative disorder, overactive disorder associated with mental retardation and stereotyped movements, Asperger's syndrome, other pervasive developmental disorders, and unspecified pervasive developmental disorder.

[3] The medicament of [1] wherein the pervasive developmental disorder is autism.

[4] A medicament for treating a genetic disease accompanied by autism-like symptoms comprising lurasidone or a pharmaceutically acceptable acid addition salt thereof.

[5] The medicament of [4] wherein the genetic disease is fragile X syndrome or phenylketonuria.

[6] A medicament for treating a congenital disease accompanied by autism-like symptoms comprising lurasidone or a pharmaceutically acceptable acid addition salt thereof.

[7] The medicament of [6] wherein the congenital disease is congenital rubella syndrome or cytomegalic inclusion body disease.

[8] The medicament of any one of [1] to [7] wherein the treatment of the disorder/disease is done by improving its core symptoms.

[9] The medicament of [8] wherein the core symptoms are impairments in social adaptive function and/or impairments in communication.

[10] The medicament of [9] wherein the impairments in social adaptive function are one or more impairments selected from the group consisting of an inadequate appreciation of socio-emotional cues, poor use of social signals, a weak integration of social, emotional, and communicative behaviors, and a lack of socio-emotional reciprocity.

[11] The medicament of [9] or [10] wherein the impairments in social adaptive function are a lack of socio-emotional reciprocity.

[12] The medicament of [9] or [10] wherein the impairments in social adaptive function are an inadequate appreciation of socio-emotional cues, and/or poor use of social signals.

[13] The medicament of any one of [9] to [12] wherein the impairments in communication are one or more impairments selected from the group consisting of impairment in make-believe and social imitative play, poor synchrony and lack of reciprocity in conversational interchange, poor flexibility in language expression, a relative lack of creativity and fantasy in thought processes, a lack of social usage of language skills, lack of emotional response to other people's verbal and nonverbal overtures, impaired use of variations in cadence or emphasis to reflect communicative modulation, and a lack of accompanying gesture to provide emphasis or aid meaning in spoken communication.

[14] The medicament of any one of [9] to [13] wherein the impairments in communication are one or more impairments selected from the group consisting of impairment in make-believe and social imitative play, poor synchrony and lack of reciprocity in conversational interchange, poor flexibility in language expression and a relative lack of creativity and fantasy in thought processes.

[15] The medicament of any one of [3] to [7] wherein the treatment of the disorder/disease is done by improving its peripheral symptoms.

[16] The medicament of [15] wherein the peripheral symptoms are one or more disorders selected from the group consisting of abnormal repetitive behavior, hyperactivity, impulsivity and irritability.

[17] The medicament of [16] wherein the peripheral symptom is irritability.

[18] The medicament of [17] wherein the irritability means one or more symptoms selected from the group consisting of aggression, self-mutilation, temper tantrum and labile mood.

[19] The medicament of any one of [1] to [18] wherein the pervasive developmental disorders are childhood pervasive developmental disorders.

[20] The medicament of any one of [1] to [19] which is used in combination with other psychotropic agent(s) usable in combination with lurasidone or a pharmaceutically acceptable acid addition salt thereof.

[21] The medicament of [20] wherein the other psychotropic agent(s) is an anxiolytic agent, an antiepileptic agent, an antidepressant, a mood-stabilizing drug, and/or an antipsychotic agent other than lurasidone.

[22] A method for treating pervasive developmental disorders which comprises administering a therapeutically effective amount of lurasidone or a pharmaceutically acceptable acid addition salt thereof to a mammal in need thereof.

[23] The method of [22] wherein the treatment of pervasive developmental disorders means the treatment of the disorder, disease or symptom defined in any one of [2] to [19].

[24] The method of [22] or [23] which also comprises administering any psychotropic agent defined in [20] or [21] in combination.

[25] Use of lurasidone or a pharmaceutically acceptable acid addition salt thereof in the manufacture of a pharmaceutical composition for treating pervasive developmental disorders.

[26] The use of a combination of
(i) lurasidone or a pharmaceutically acceptable acid addition salt thereof and
(ii) any psychotropic agent defined in [20] or [21] in the manufacture of a pharmaceutical composition for treating pervasive developmental disorders.

[27] The use of [25] or [26] wherein the treatment of pervasive developmental disorders means the treatment of the disorder, disease or symptom defined in any one of [2] to [19].

[28] A pharmaceutical composition comprising lurasidone or a pharmaceutically acceptable acid addition salt thereof for use in the treatment of pervasive developmental disorders.

[29] A pharmaceutical composition comprising
(i) lurasidone or a pharmaceutically acceptable acid addition salt thereof and
(ii) any psychotropic agent defined in [20] or [21] for use in the treatment of pervasive developmental disorders.

[30] The pharmaceutical composition of [28] or [29] wherein the treatment of pervasive developmental disorders means the treatment of the disorder, disease or symptom defined in any one of [2] to [19].

[31] A pharmaceutical product for treating pervasive developmental disorders comprising lurasidone or a pharmaceutically acceptable acid addition salt thereof.

[32] A pharmaceutical product for treating pervasive developmental disorders comprising
(i) lurasidone or a pharmaceutically acceptable acid addition salt thereof and
(ii) any psychotropic agent defined in [20] or [21].

[33] The pharmaceutical product of [31] or [32] wherein the treatment of pervasive developmental disorders means the treatment of the disorder, disease or symptom defined in any one of [2] to [19].

[34] A kit for treating pervasive developmental disorders comprising lurasidone or a pharmaceutically acceptable acid addition salt thereof.

[35] A kit for treating pervasive developmental disorders comprising
(i) lurasidone or a pharmaceutically acceptable acid addition salt thereof and
(ii) any psychotropic agent defined in [20] or [21].

[36] The kit of [34] or [35] wherein the treatment of pervasive developmental disorders means the treatment of the disorder, disease or symptom defined in any one of [2] to [19].

Effect of the Invention

Lurasidone or a pharmaceutically acceptable acid addition salt thereof of the present invention is useful for treating pervasive developmental disorders and autism, in particular, has an effect for improving core symptoms (impairments in social adaptive function and impairments in communication) in pervasive developmental disorders and autism.

Furthermore, lurasidone or a pharmaceutically acceptable acid addition salt thereof of the present invention is also useful for treating peripheral symptoms in pervasive developmental disorders and autism such as abnormal repetitive behavior, hyperactivity, impulsivity, and irritability, in particular, irritability.

Lurasidone or a pharmaceutically acceptable acid addition salt thereof of the present invention is also expected to exhibit the therapeutic effect for other symptoms such as anxiety disorder, depressive symptom, and mood disorder which are often accompanied with pervasive developmental disorders and autism.

In addition, the present invention is also expected to have an effect for improving impairments in social adaptive function and impairments in communication in patients of schizophrenia and/or bipolar disorder.

DESCRIPTION OF EMBODIMENTS

Figure 1:
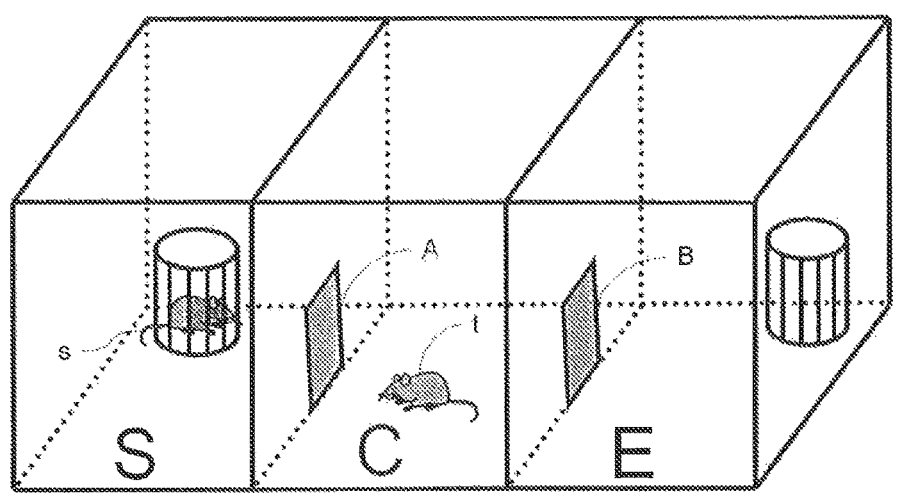
FIG. 1 schematically shows a test mouse (t: test mouse), a box for the 3-chambered social interaction test in Example 1 (test box) that has three adjacent chambers, i.e., a central chamber (C: center) in which the mouse is to be put at the first set out, a chamber (S: stranger side) equipped with a small cage for enclosing the same-aged/same-lined stranger mouse (s: stranger) which is unfamiliar to the test mouse (t), and a chamber (E: empty side) equipped with a small empty cage, and each dividing wall with each openable/closable doors (A and B) between the adjacent chambers.

Lurasidone may be used in form of the free base, optionally in form of its pharmaceutically acceptable acid addition salt and/or optionally in form of the hydrate and/or solvate thereof. Suitable acid addition salts include, for example, those of the acids selected from succinic acid, hydrobromic acid, acetic acid, fumaric acid, maleic acid, methanesulphonic acid, lactic acid, phosphoric acid, hydrochloric acid, sulphuric acid (sulfuric acid), tartaric acid and citric acid. Mixtures of the above-mentioned acid addition salts may also be used. Among the aforementioned acid addition salts the hydrochloride and the hydrobromide, particularly the hydrochloride, are preferred.

The present invention includes within its scope prodrugs of lurasidone or a pharmaceutically acceptable acid addition salt thereof. Such prodrugs are functional derivatives of the compound of the present invention (lurasidone) which are readily convertible in vivo into the required compound (lurasidone).

The specific prodrugs of the invention can be prepared, but are not limited to, for example, by means disclosed in *Nature Reviews Drug Discovery* 7; 255-270 (2008); or WO 2011/084850 A1. Or, the specific prodrugs of the invention can also be prepared, but are not limited to, for example, by means disclosed in WO 2012/0651.02 A2; WO 2012/065110 A2; WO 2012/088441 A1; or WO 2013/016727 A1.

The term "therapeutically effective amount" means the amount of a drug or pharmaceutical agent that will elicit the biological or medical response of a tissue, system, animal or human that is being sought by a researcher or clinician.

The terms "treating" and "treatment" used herein include any treatment of the disease (e.g. improvement of the symptoms, relief of the symptoms, arrest of the development of the symptoms, etc.).

As used herein, the term "pharmaceutical product" is intended to encompass a product comprising specified ingredients in each specified amount, as well as any product which results, directly or indirectly, from combination of specified ingredients in each specified amount.

The term "childhood" used herein means the period of 0 year to about 15 years old (e.g., 13 to 17 years old). In particular, the "child" used herein means a patient of an age within the above childhood, suitable for administering the medicament of the present invention, taking into consideration his or her symptoms, benefit for treatment and/or safety, when using for treating pervasive developmental disorders, autism and the like in the present invention, which includes a patient of, for example, 3 to 17 years old, preferably 5 to 17 years old, more preferably 5 to 16 years old or 6 to 17 years old.

The term "pervasive developmental disorders" used herein means a group of disorders characterized by qualitative abnormalities in reciprocal social interactions and in patterns of communication, and by restricted, stereotyped, repetitive repertoire of interests and activities. According to International Statistical Classification of Diseases and Related Health Problems (ICD-10), the pervasive developmental disorders include childhood autism ("autism" in ICD-10), atypical autism, Rett's syndrome (Rett syndrome), other childhood disintegrative disorder, overactive disorder associated with mental retardation (or intellectual disability) and stereotyped movements, Asperger's syndrome (Asperger syndrome), other pervasive developmental disorders, and unspecified pervasive developmental disorder. These days, the above-mentioned diseases included in pervasive developmental disorders are called "autism spectrum" or "autistic spectrum" as a factor of continuum of pervasive developmental disorders. And herein, the above-mentioned diseases included in pervasive developmental disorders may be also written as "autism and the like".

The term "autism" used herein means a pervasive developmental disorder defined by the presence of abnormal and/or impaired development that is manifest before the age of 3 years, and by the characteristic type of abnormal functioning in all three areas of (reciprocal) social interaction, communication, and restricted, repetitive behavior. The autism defined in ICD-10 (childhood autism) is further classified into 6 kinds of diseases: Kanner syndrome, high-functioning autism, child psychosis, childhood autism, infantile autism, and infantile psychosis, all of which are included in the "autism" of the present invention. Patients of autism can suffer from core symptoms such as impairments in social adaptive function and impairments in communication, and peripheral symptoms such as abnormal repetitive behavior, hyperactivity, impulsivity and irritability.

The term "impairments in social adaptive function" used herein means qualitative impairments in reciprocal social interaction which are always observed in patients of autism. More specifically, the "impairments in social adaptive function" as core symptoms of autism include, for example, inadequate appreciation of socio-emotional cues (for example, as shown by a lack of responses to other people's emotions and/or a lack of modulation of behavior according to social context), and poor use of social signals. Or, the "impairments in social adaptive function" include a weak integration of social, emotional, and communicative behaviors, in particular, a lack of socio-emotional reciprocity.

The term "impairments in communication" used herein means qualitative impairments in communication which are always observed in patients of autism. The "impairments in communication" as core symptoms of autism include, for example, impairment in make-believe and social imitative play, poor synchrony and lack of reciprocity in conversational interchange, poor flexibility in language expression, and a relative lack of creativity and fantasy (imagination) in thought processes. Or, the "impairments in communication" include a lack of social usage of whatever language skills are present, lack of emotional response to other people's verbal and nonverbal overtures, impaired use of variations in cadence or emphasis to reflect communicative modulation, and a similar lack of accompanying gesture to provide emphasis or aid meaning in spoken communication.

The core symptoms of autism (impairments in social adaptive function and impairments in communication) are also observed in general pervasive developmental disorders which are broader concept thereof, or autistic spectrum. Hence, in core symptoms of pervasive developmental disorders, impairments in social adaptive function and impairments in communication are also observed like the above-mentioned core symptoms in autism.

As the peripheral symptoms of autism, in more detail, the abnormal repetitive behavior includes insisting on the performance of particular routines in rituals of a nonfunctional character, and the preoccupation with interests such as dates, routes or timetables; the behavior disorder in hyperactivity and impulsivity includes running and jumping around when he or she is supposed to remain seated, and excessive talkativeness; and the behavior disorder in irritability includes aggression toward the self and others; etc. In particular, "irritability" which is one of the peripheral symptoms in autism is also called as "easy-irritancy" or "excitement related to autistic disease", which means a state over-reactive to irritation, and includes, for example, aggression, self-mutilation (self-injury), temper tantrum, and quickly changing moods. For example, irritability is a symptom with which autism mainly in childhood (e.g., 6 to 17 years old) or school-age period to adolescence (e.g., 5 to 16 years old) is accompanied.

The term "genetic disease" used herein means an inheritable disease caused by the abnormality of gene or chromosome, which is sometimes accompanied with an autism-like symptom. Such genetic disease includes fragile X syndrome and phenylketonuria which may be also accompanied with the above-mentioned autism-like symptom including core symptoms and peripheral symptoms.

The term "congenital disease" used herein includes the above-mentioned genetic diseases caused by the abnormality of gene or chromosome, as well as congenital infection in embryonic stage which is caused by virus (rubella, cytomegalovirus, coxsackievirus, etc.) in mother's body, and furthermore a disease caused by maternal environmental factor (e.g. alcohol, medicament, diabetes in mother body, etc.). Congenital disease is a general term that means diseases of inherent abnormality in the shape and function of important organs such as heart and brain, which may be accompanied with an autism-like symptom. Congenital disease includes congenital rubella syndrome, cytomegalic inclusion body disease, and the like, which may be also accompanied with the above-mentioned autism-like symptom including core symptoms and peripheral symptoms.

In the present invention, the degree of improvement in core symptoms (impairments in social adaptive function and impairments in communication) in pervasive developmental disorders and autism can be assessed, for example, using Childhood Autism Rating Scale (CARS) and Autism Diagnostic Observation Schedule-Generic (ADOS-G) as clinical indicators.

In the present invention, the degree of improvement in each symptom (core symptoms and peripheral symptoms) in pervasive developmental disorders and autism can be also assessed using clinical indicators such as Rimland Questionnaires, Expressive Vocabulary Test, Social Responsiveness Scale and the like, besides the aforementioned CARS and ADOS-G.

In case that lurasidone or a pharmaceutically acceptable acid addition salt thereof of the present invention is used in combination with other usable medicament(s), these medicaments may be administered separately or together in one pharmaceutical composition. In addition, the administration of one active ingredient of the combination of the present invention may be prior to, concurrent with, or subsequent to the administration of the other active ingredient(s) of the combination. These active ingredients may be formulated into a single dosage form or separate ones.

The other medicament usable in combination with lurasidone or a pharmaceutically acceptable acid addition salt thereof of the present invention includes, as a preferred example, another psychotropic agent such as anxiolytic agent, antiepileptic agent, antidepressant, mood-stabilizing drug, and antipsychotic agent. Among the above other psychotropic agents usable in combination, anxiolytic agent, antiepileptic agent, antidepressant, and mood-stabilizing drug are preferable; in more detail, the agents include diazepam, tandospirone and the like as anxiolytic agent; carbamazepine, zonisamide and the like as antiepileptic agent; fluoxetine, paroxetine and the like as antidepressant; and lithium carbonate and the like as mood-stabilizing drug.

In addition, lurasidone or a pharmaceutically acceptable acid addition salt thereof of the present invention is known itself as an antipsychotic agent, but an antipsychotic agent other than lurasidone (aripiprazole, risperidone, haloperidol, clozapine, olanzapine, and the like) may be used in the combination. Lurasidone of the present invention has a unique effect for improving core symptoms (impairments in social adaptive function and impairments in communication), and the effect has not been observed yet in case of any other antipsychotic agents. Thus, the combination of lurasidone and other antipsychotic drug(s) such as aripiprazole and risperidone which are known to improve irritability that is one of peripheral symptoms in autism is expected to have the multiple therapeutic effects for core symptoms and peripheral symptoms, and the enhanced therapeutic effect for peripheral symptoms.

Lurasidone of the present invention can readily form a salt thereof by treating with a pharmaceutically acceptable acid. The acid includes an inorganic acid such as hydrochloric acid, sulphuric acid (sulfuric acid), phosphoric acid, and hydrobromic acid; and an organic acid such as oxalic acid, maleic acid, fumaric acid, malic acid, tartaric acid, citric acid, and benzoic acid. A preferable salt of lurasidone includes the hydrochloride thereof.

The active ingredient of the present invention (lurasidone or a pharmaceutically acceptable acid addition salt thereof) may be administered by oral, parenteral (e.g., intramuscular, intraperitoneal, intravenous or subcutaneous injection, or implant), buccal, nasal, vaginal, rectal, sublingual, or topical (e.g., ocular eyedrop) routes of administration and may be formulated alone or together with other usable medicament(s), in suitable dosage unit formulations containing conventional non-toxic pharmaceutically acceptable carriers, adjuvants and vehicles appropriate for each route of administration.

The term "kit" used herein means a set of drug formulation comprising active ingredients and other ingredients for formulation, which may optionally equipped with a device necessary for administration (e.g. syringe, cartridge, vial, aerosol, etc.) to adjust the administration amount, and thereby can allow its end-user to administer it for him or herself.

The active compound of the present invention, i.e. lurasidone, and a pharmaceutically acceptable acid addition salt thereof can be orally administered in a tailored amount of the active ingredient, as a generally-used dosage form which is a pharmaceutical product suitable for oral administration such as tablet, capsules, syrup, and suspension, or as another pharmaceutical product, parenterally administered as a liquid form such as solution, emulsion and suspension with an injection or a patch.

The above-mentioned dosage form can be prepared by formulating the active compound with conventional additives such as carrier, excipient, binder, and stabilizer. In the case of injections, for example, acceptable buffer, solubilizer, isotonic agent and pH adjuster can be also used.

The dosage of the active ingredient of the present invention is not limited, but the therapeutic dosage and frequency of administration can vary depending upon administration form or severity of the disease condition requiring treatment. For example, lurasidone or a pharmaceutically acceptable acid addition salt thereof of the present invention can be orally administered in a dosage of 1-200 mg, preferably 20-160 mg, per day for an adult, and once to several times a day. And, for example, when lurasidone or a pharmaceutically acceptable acid addition salt thereof of the present invention is used for a child, the dosage can be decided, based on its body weight considering above-mentioned adult dosage. For example, lurasidone or a pharmaceutically acceptable acid addition salt thereof can be orally administered in a dosage of 1-160 mg, preferably 10-120 mg, more preferably 20-120 mg, per day for a child, and once to several times a day.

When lurasidone or a pharmaceutically acceptable acid addition salt thereof as the active ingredient is prepared in a dosage form (drug formulation, or pharmaceutical composition), or when lurasidone or a pharmaceutically acceptable acid addition salt thereof is prepared in a single dosage form in combination with other medicament(s), the whole pharmaceutical composition (the dosage form) may include the sum of the active ingredient(s) in 0.1-70% (w/w), preferably 5-40% (w/w) per the whole preparation (pharmaceutical composition), but not limited thereto.

EXAMPLE

Hereinafter, the present invention is further illustrated by Examples, but should not be construed to be limited thereto.

Example 1

(Method)

It is known that a mouse given phencyclidine (PCP: 1-(1-phenylcyclohexyl)piperidine; a glutamate receptor antagonist) exhibits social withdrawal symptom (i.e., a social-interaction-decreased mouse induced by PCP, or a PCP-treated mouse) (Reference 1-(1): Psychopharmacology, 1995, 120, 67-74). In addition, 3-chambered social interaction test is a test for evaluating the social interaction in mice, which is also known as a test for evaluating core symptoms (impairments in social adaptive function and impairments in communication) which are observed in pervasive developmental disorders, in particular, autism (Reference 1-(2): Genes, Brain and Behavior, 2004, 3, 287-302). The present inventor assumed that it is possible to validly evaluate the therapeutic effect for pervasive developmental disorders and autism by applying a social-interaction-decreased mouse induced by PCP (PCP-treated mouse) to the 3-chambered social interaction test, and then carried out the following experiment.

The social-interaction-decreased mouse induced by PCP which is used herein was prepared by modifying the conditions described in the above-mentioned Reference 1-(1), as follows. To 9-11 ICR mice per group (5 weeks old to 7 weeks old, Japan SLC Inc.), a 1 mg/mL injection solution of PCP in saline was subcutaneously administered at a dose of 10 mg/kg, twice a day, for three days.

The 3-chambered social interaction test which is used herein was prepared and carried out, based on the method described in the above-mentioned Reference 1-(2), and by partially modifying the conditions thereof, specifically as follows. In an animal experiment room, a box for the test (test box) is set (see, FIG. 1), which has a central chamber (C: center) and two other chambers attached adjacently to each end side of the central chamber, i.e., one is a chamber (S: stranger side) equipped with a small cage for enclosing the same-aged/same-lined stranger mouse (s: stranger) which is unfamiliar to a test mouse (t: test mouse) and the other one is a chamber (E: empty side) equipped with a small empty cage, and each dividing wall between the adjacent chambers has each openable/closable door (A and B). The day before the test, a mouse which is to be used as the same-aged/same-lined stranger mouse (s) in the test was enclosed and habituated in the above-mentioned small cage for 1 hour.

The test mouse (t) in a breeding cage was moved, staying in the cage, to an animal experiment room in which the illuminance is 20 lux, and habituated for 1 hour there. Lurasidone hydrochloride which is a compound to be evaluated was suspended in 0.5% methylcellulose (MC), and the concentration thereof was adjusted to be a suspension for administration (10 mL/kg). One hour before starting the test, a vehicle (0.5% MC, which is the same volume as the drug-administered groups) or the suspension of lurasidone hydrochloride (the administration amounts are 0.3 mg/kg and 1.0 mg/kg, respectively for 2 groups) were forcedly orally administered to each test mouse (t) to create a vehicle-administered group and drug-administered groups (the above-mentioned 2 groups), respectively. Five minutes before starting the test, the test mouse (t) was habituated in the above-mentioned test box in which the doors (A and B) were opened. In the habituation process, the same-aged/same-lined stranger mouse (s) is not set in the test box. Then, the test mouse (t) was turned in the central chamber (C), the doors (A and B) were closed, and the same-aged/same-lined stranger mouse (s) was set in the small cage of the test box. On starting the test, the closed doors (A and B) between the central chamber (C) and each chamber adjacent to the central chamber (S and E) were opened again. For 10 minutes after starting the test, the each time that the test mouse spent in the each chamber (C, S and E) was automatically measured and the data was analyzed, both of which were carried out with a camera-equipped image analysis software platform (EthoVision, Noldus).

When mice did not move into either side chamber (S or E) during the test time of 10 minutes, the result of the mice was judged to be inadequate and the data was excluded from the experimental analysis.

(Result)

In the 3-chambered social interaction test, a mouse generally tends to spend longer time in chamber (S) with the same-aged/same-lined stranger mouse (s) than in the empty chamber (E) because a normal mouse is an animal having a strong preference for social interaction. However, the above-mentioned PCP-treated mouse (a social-interaction-decreased mouse induced by PCP) shows lower social interaction, hence the mouse is expected to spend longer time in the empty chamber (E). As shown in left half of the results in FIG. 2, the normal mouse which was not treated with PCP (of vehicle-administered group) spent significantly longer time in chamber (S) where the same-aged/same-lined stranger mouse (s) was set than in the empty chamber (E) (Student's t-test: $P<0.05$). However, in the test with the PCP-treated mouse (of vehicle-administered group), there was no significant difference in the spent time between both of the chambers (S and E). Based on these results, it was confirmed that the social interaction of an ICR mouse can be lowered by administering PCP to the mouse and the present test system can be a model having core symptoms in pervasive developmental disorders and autism.

Figure 2:
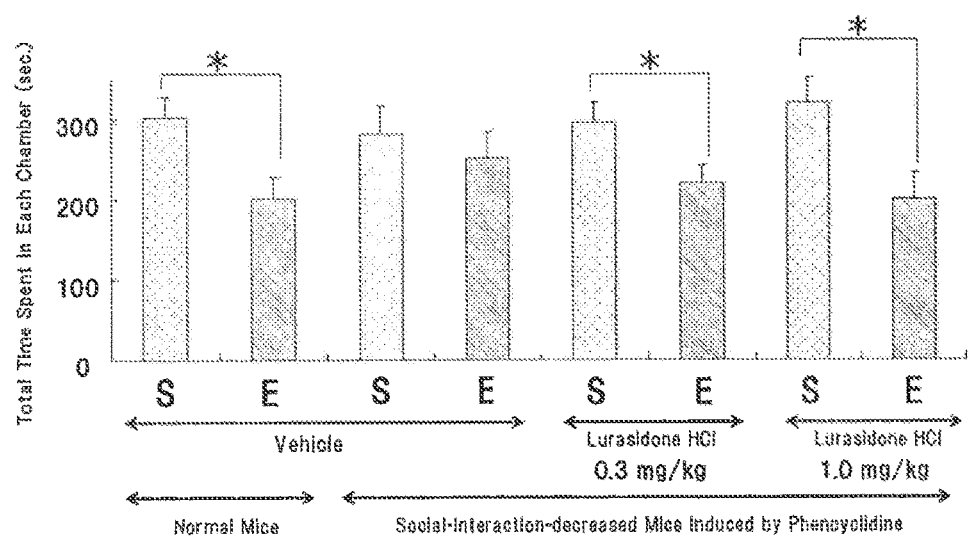
FIG. 2 shows each total time (sec.: seconds) spent by each test mouse in the chamber (S) with the same-aged/same-lined stranger mouse (s) and the empty chamber (E) when lurasidone hydrochloride (lurasidone HCl) was orally administered to a social-interaction-decreased mouse induced by phencyclidine (PCP) (2 groups, 0.3 mg/kg and 1.0 mg/kg) and 1 hour later the 3-chambered social interaction test in Example 1 was carried out. The left half of the experimental results shows each result in the vehicle-administered groups with normal mice and social-interaction-decreased mice induced by PCP, and the right half of the experimental result shows results in the drug-administered group (wherein drug is lurasidone hydrochloride) with social-interaction-decreased mice induced by PCP. Each bar graph shows a mean value of the results in each group, and the symbol * denotes that the level of significance (P value) is less than 0.05 based on Student's t-test.

And, as shown in right half of the results in FIG. 2, mice in both the drug-administered groups, wherein lurasidone hydrochloride (lurasidone HCl) was administered to social-interaction-decreased mice induced by PCP (i.e., PCP-treated mice) in a dose of 0.3 mg/kg and 1.0 mg/kg, spent significantly longer time in chamber (S) where the same-aged/same-lined stranger mouse (s) was set than in the empty chamber (E) (Student's t-test: $P<0.05$). In addition, the administration of lurasidone hydrochloride in a dose of 1.0 mg/kg restored the social-interaction-decreased mice induced by PCP (the PCP-treated mice) to a normal level of social interaction. The decrease of social interaction in the present mouse experimental model is equivalent to core symptoms (impairments in social adaptive function and impairments in communication) in pervasive developmental disorders and autism. According to the result of the test, it has been found that lurasidone hydrochloride can improve core symptoms (impairments in social adaptive function and impairments in communication) in pervasive developmental disorders and autism and thereby can treat these diseases.

Example 2

Besides the above method, according to the method in the following Reference 2-(1), Reference 2-(2) or a similar method thereof as a test method with animal model for assessing each symptom in autism (core symptoms and peripheral symptoms), it is possible to assess the effect of lurasidone or a pharmaceutically acceptable acid addition salt thereof for improving each symptom in autism (core symptoms and peripheral symptoms).

Reference 2-(1): Neuropsychopharmacology, 2010, 35, 976-989.

Reference 2-(2): Cell, 2011, 147, 235-246.

Example 3

As a clinical test suitable for assessing each symptom in autism (core symptoms and peripheral symptoms), Autistic Diagnostic Observation Schedule-Generic, Rimland Questionnaires, Expressive Vocabulary Test (see below, Reference URL1) can be used to assess the effect of the compound in the present invention (i.e., lurasidone or a pharmaceutically acceptable acid addition salt thereof) for improving each symptom in autism.

Reference URL1 http://clinicaltrials.gov/ct2/show/NCT00065962?term=synthetic+porcine+autism&rank=1

Example 4

As a clinical test suitable for assessing each symptom in autism (core symptoms and peripheral symptoms), the test method disclosed in the following Reference 4-(1) or Reference 4-(2), or a similar method thereof can be used to assess the effect of the compound in the present invention (i.e., lurasidone or a pharmaceutically acceptable acid addition salt thereof) for improving each symptom in autism.

Reference 4-(1): Journal of Autism and Developmental Disorders, 1980, 10(1), 91-103.

Reference 4-(2): Journal of Autism and Developmental Disorders, 2002, 32(6), 593-599.

In more detail, for patient population which is adapted to the criterion of autism in, for example, DSM-IV-TR (Diagnostic and Statistical Manual of Mental Disorders, 4th. Edition, Text Revision) or ICD-10 (The ICD-10 Classification of Mental and Behavioural Disorders Clinical descriptions and diagnostic guidelines), the effect for improving each symptom in autism can be assessed by continuing the administration of the compound in the present invention for a certain period (for example, 36 weeks, but not limited thereto) and comparing both the total scores of Childhood Autism Rating Scale (CARS) between before/after the administration period.

In the above test, it is possible to optionally modify/change the conditions such as patient population, administration period, doses of the drug, and investigational methods. For example, besides the total score of Autistic Diagnostic Observation Schedule-Generic, an assessment through the score of Social Responsiveness Scale and/or Expressive Vocabulary Test can be used. In addition, other test methods disclosed in Reference 4-(1) or Reference 4-(2), and other test methods cited therein, and further modified methods thereof can be also used.

Example 5

It is known that some non-human primates such as rhesus macaques and cynomolgi can have a communication through joint visual attention (JVA), like humans. In particular, common marmosets are relatively-small but also known as a non-human primate which can have a communication through JVA. The "joint visual attention (JVA)" is a behavior to look at where one is looking or pointing, and it is also referred to as "conjugate gaze". It is thought that the decline in the ability of JVA is associated with the avoidance of eye contact (i.e., lack of conjugate gaze) which is one of symptoms specific to autism, especially which is thought to be intimately-associated with the core symptoms in autism. In addition, it has been reported in clinical and non-clinical tests that the administration of an NMDA antagonist (e.g. ketamine, PCP, MK-801, etc.) can decrease cognitive function. In particular, it is known that the administration of ketamine to a common marmoset decreases the ability of JVA (JVA ability).

Accordingly, it is possible to evaluate the therapeutic effect for autism with the compound of the present invention (i.e., lurasidone or a pharmaceutically acceptable acid addition salt thereof) by testing the compound of the present invention with the following method.

Using a common marmoset as a test animal which is one of non-human primates, ketamine which is an NMDA antagonist is administered to the test animal to decrease the ability of JVA. A favorite food of the test animal as a reward is put in one of plural boxes to be hidden from the animal. A researcher makes eye contact with the test animal and then points at the box containing the reward (reward box) with the researcher's finger among plural boxes while keeping the eye contact (the researcher's eyes may naturally turn to the reward box in response to the eye motion of the test animal). Thus, the researcher provides the test animal with his/her suggestion by means of both his/her eye contact and pointing with his/her finger. The number of empty boxes in which the test animal has been interested before finding the reward is counted (number of counts). Based on the number of counts, a scoring system is made so that the score should be evaluated to be lower when the number of counts is more. Thus, the scoring system makes it possible to evaluate the level of JVA ability. The box used herein is designed as a test animal cannot see whether there is a reward in the box, from the front (the animal's position), but can take out the reward with its own hands, without opening or breaking, when there is a reward in the box. Before beginning the test, a reward food is served to a test animal by giving the above boxes all of which contain the food, in order to have the test animal recognize that there could be a reward food in the box. The dose of an NMDA antagonist (ketamine) is decided so that the test animal is awake, the animal can recognize an object, and the ability of JVA in the animal is decreased. To the test animal whose score based on the above-mentioned scoring system is lowered by administering an NMDA antagonist (ketamine), lurasidone or a pharmaceutically acceptable acid addition salt thereof is administered, and then the level of JVA ability is evaluated as mentioned above. Analyzing the improvement of the score as an indicator, it is possible to evaluate the therapeutic effect for autism with lurasidone or a pharmaceutically acceptable acid addition salt thereof.

Example 6

The spontaneous alternation behavior test (Y-maze test) and the elevated plus maze test, using juvenile stroke-prone spontaneously hypertensive rats (juvenile SHRSP) are behavioral pharmacological tests for evaluating attentional function and hyperactivity by the former test and evaluating impulsivity by the latter test, respectively, which are thought to intimately relate to symptoms in autism, in particular peripheral symptoms thereof. Thus, these tests make it possible to evaluate the therapeutic effect for autism, in particular the improvement effect for peripheral symptoms thereof, with lurasidone or a pharmaceutically acceptable acid addition salt thereof.

The invention claimed is:
1. A method for treating at least one core symptom in autism, comprising:
 administering a therapeutically effective amount of lurasidone or a pharmaceutically acceptable acid addition salt thereof as a sole active ingredient to a mammal in need thereof,
 wherein the at least one core symptom is at least one of impairment in social adaptive function and impairment in communication.
2. The method of claim 1, wherein the at least one core symptom is impairment in social adaptive function.
3. The method of claim 1, wherein the at least one core symptom is impairment in communication.

* * * * *